US010190951B2

(12) United States Patent
Clavaguera et al.

(10) Patent No.: US 10,190,951 B2
(45) Date of Patent: Jan. 29, 2019

(54) ASSEMBLY FOR PICKING AND TRANSPORTING NANOOBJECTS CONTAINED IN AEROSOLS, WITH A CASSETTE THE OPENING OF WHICH IS SECURED DURING THE PICKING

(71) Applicants: COMMISSARIAT A L'ENERGIE ATOMIQUE ET AUX ENERGIES ALTERNATIVES, Paris (FR); NANOINSPECT, Peronnas (FR)

(72) Inventors: Simon Clavaguera, Grenoble (FR); Christophe Brouard, Grenoble (FR); Guillaume Hebert, La Tronche (FR); Eric Decolin, Montbonnot Saint Martin (FR); Raphael De Thoury, Croissy-Beaubourg (FR); Bertrand Faure, Grenoble (FR)

(73) Assignees: COMMISSARIAT A L'ENERGIE ATOMIQUE ET AUX ENERGIES ALTERNATIVES, Paris (FR); PARTICLEVER, Paris (FR)

( * ) Notice: Subject to any disclaimer, the term of this patent is extended or adjusted under 35 U.S.C. 154(b) by 0 days.

(21) Appl. No.: 15/315,853

(22) PCT Filed: Jun. 3, 2015

(86) PCT No.: PCT/IB2015/054209

§ 371 (c)(1),
(2) Date: Dec. 2, 2016

(87) PCT Pub. No.: WO2015/186081

PCT Pub. Date: Dec. 10, 2015

(65) Prior Publication Data

US 2017/0097287 A1 Apr. 6, 2017

(30) Foreign Application Priority Data

Jun. 4, 2014 (FR) .................................... 14 55051

(51) Int. Cl.
*G01N 1/22* (2006.01)

(52) U.S. Cl.
CPC ... *G01N 1/2205* (2013.01); *G01N 2001/2223* (2013.01); *G01N 2001/2288* (2013.01)

(58) Field of Classification Search
CPC .................................................. G01N 1/2205
USPC ........................................................ 422/534
See application file for complete search history.

(56) References Cited

U.S. PATENT DOCUMENTS 4,961,916 A 10/1990 Lesage et al.
4,965,955 A * 10/1990 Campbell ............. A01K 63/02
119/201

(Continued)

FOREIGN PATENT DOCUMENTS

DE 10 2006 018 347 A1 10/2007
EP 1 327 133 B1 7/2003

(Continued)

OTHER PUBLICATIONS

International Search Report for PCT/IB2015/054209 dated Aug. 19, 2015.

*Primary Examiner* — Jill A Warden
*Assistant Examiner* — Jacqueline Brazin
(74) *Attorney, Agent, or Firm* — Jones Robb, PLLC

(57) ABSTRACT

An assembly for picking and transporting nano-objects, comprises a cassette having first and second components, which are provided with means of mutual assembly and with means for holding the filter. The first and second components define, when the components are in an assembled configuration, a cavity in which the filter is housed and held therein. The means of mutual assembly comprise first clipping means secured to the first component, second clipping means secured to the second component and able to collaborate with the first clipping means so as to clip the two (Continued)

components together. A picking device comprises suction means to which the cassette is able to be removably attached. The first and second clipping means are configured such that they are not accessible from the outside when the components are in the assembled configuration with the cassette fixed to the device.

7 Claims, 4 Drawing Sheets

(56) References Cited

U.S. PATENT DOCUMENTS

| | | | |
|---|---|---|---|
| 5,205,155 A | 4/1993 | Cooper | |
| 2008/0196514 A1 | 8/2008 | Kenny | |
| 2009/0272202 A1 | 11/2009 | Uang et al. | |
| 2011/0150724 A1* | 6/2011 | Furle | G01N 35/0099 |
| | | | 422/549 |
| 2012/0134895 A1* | 5/2012 | Kanda | G01N 1/405 |
| | | | 422/534 |
| 2014/0286836 A1 | 9/2014 | Clavaguera et al. | |
| 2015/0251119 A1 | 9/2015 | Clavaguera et al. | |

FOREIGN PATENT DOCUMENTS

| | | |
|---|---|---|
| FR | 2981154 A1 | 4/2013 |
| WO | 2014/001936 A1 | 1/2014 |
| WO | WO 2014001936 * | 1/2014 |
| WO | 2014081314 A1 | 5/2014 |
| WO | WO 2014081314 * | 5/2014 |

* cited by examiner

ASSEMBLY FOR PICKING AND TRANSPORTING NANOOBJECTS CONTAINED IN AEROSOLS, WITH A CASSETTE THE OPENING OF WHICH IS SECURED DURING THE PICKING

This application is a national stage application of International PCT Application No. PCT/IB2015/054209, filed internationally on Jun. 3, 2015, which claims priority to French Application No. FR 14 55051, filed Jun. 4, 2014, the entire content of each of which is incorporated by reference herein in its entirety.

TECHNICAL FIELD

The present invention concerns the field of collection and analysis of nanoparticles susceptible of being present in suspension in the air.

More particularly, it concerns the design of an assembly for sampling and transporting of nano-objects contained in aerosols, with a sampling cassette. The present invention proposes to improve the securing of the opening of such a cassette in order to guarantee the integrity of the sampling.

PRIOR ART

The rapid rise of nanotechnologies is making it necessary to look into the health and environmental impacts of these new materials in order to have optimal safety conditions. For several years, nanoparticles, or particles with nanometer dimensions, have been the subject of intense research and their use has begun to spread into various fields such as health, microelectronics, energy technologies or ordinary consumer products such as paints and cosmetics. It is therefore necessary to create methods for evaluation and monitoring of the exposure of workers, consumers and the environment to nanoparticles.

The development of reliable methods of sampling and analysis of aerosols is thus a crucial issue in terms of public health and prevention of risks at workstations. In particular, the development of sampling devices adapted to be portable and secured as a unit to the work clothes of a worker at a station for the manufacture of nano-objects or the processing of nano-materials might prove to be mandatory.

The method of choice for sampling, or the one which is preferred at present, consists in aspirating a flow of air liable to be laden with particles through a filter which is then analyzed by various techniques (gravimetry, microscopy, XRF, etc.).

In the prior art, sampling devices also known as cassette samplers are already known, these being portable and having to sample an aerosol contamination liable to be inhaled through the mouth and the nose of an individual during his respiration.

A sampler is a device which comprises in particular means of aspiration and on which is secured, generally in removable manner, a sampling cassette holding at least one filter for sampling of contaminants by aspiration.

Thus, the U.S. Pat. No. 4,961,916 concerns a sampling device for gaseous and particulate pollutants comprising a cassette inside which three filters are stacked one on top of the other and comprising two openings on either side of these filters, one of them emerging into the outside environment liable to be polluted and the other one emptying into a pipe connected to a suction pump. Thus, from upstream to downstream, during the aspiration by the pump, the first filter enables collecting of only the particulate fraction of the aerosol, the second filter, previously impregnated with a reagent, enables a selective reaction with one or more gaseous compounds, and the third filter only has the function of stiffening the filter assembly. The sampling with which this patent is concerned is the collection of gaseous and particulate isocyanates which are present in polluted air.

The U.S. Pat. No. 5,205,155 for its part discloses a sampling device for asbestos fibers liable to be in suspension in the air and its concern is the nonuniform deposition on the filter housed in the sampling cassette. As a remedy, the patent proposes designing the inlet of the cassette, that is, the one near the aspiration orifice of the particular environment, in a flared shape and making it smooth so as to promote a homogeneous deposition of particles on the filter.

Patent application US 2008/0196514A1 concerns an individual sampling device for dust, used to collect the inhalable fraction of airborne particles. This patent describes various shape ratios of the cassette (ratios between length L and inlet diameter D of the opening) which, according to it, allow an improvement in the sampling by aspiration. What is more, this patent mentions that, for the most representative nature of the inhalation through the nose, it is advantageous to provide a vertical orientation of the air flow aspirated from bottom to top.

Patent application US 2009/0272202A1 concerns an individual sampling device for nanoparticles comprising a cassette with different stages of selection of particles depending on their size. The disclosed device comprises an assembly bringing together the different stages with assembly plates held together by springs and guide rods used for guidance during the assembly process.

All the methods and devices for sampling of aerosols in the prior art, as described, have one or more major drawbacks, which can be summarized as follows:

the majority of the sampling methods for aerosols require an extraction of the filter from its cassette in situ, that is, at the place of the sampling. The implementing devices are thus designed for the cassette to be opened easily and by anyone at all: thus, an opening with untimely extraction may result in contamination external to the filter, in a loss of material adsorbed onto the filter or in a poor traceability of the filter. In particular, a worker at a manufacturing station for nano-objects or processing of nano-materials may open a cassette in untimely manner, contaminate a filter, put back a filter already used, etc.

all the cassettes in sampling configuration, that is, a configuration secured to the sampling device (sampler), can still be opened by the worker, because they are accessible from all parts. This does not allow a sampler to be left unattended with groups of workers not authorized for its opening, without the certainty that the cassette has not been disassembled and thus that the analysis of the sample/the sampling is afterwards invalidated.

The inventors of the present application have proposed, in patent application FR 2981154, a two-piece sampling cassette, the pieces of which are assembled by clipping means not accessible from the outside. Thus, these clipping means can only be physically accessed through pins individually lodged in holes, but this cannot be done manually or by using just any tool from the space from outside the cassette in the configuration with the two pieces assembled together. Thanks to the clipping means, the cassette is thus secured, since it cannot be opened in untimely manner, as its opening for the actual analysis of the sample requires an adequate tool to separate the two pieces of the cassette.

While this securing of the opening of the cassette is perfectly adequate in the majority of situations, the inventors nevertheless determined that there still existed a situation of untimely opening, in the case when an unauthorized person might have pins for disassembling the two pieces of the cassette from each other. In other words, there still exists a risk of opening of the sampling cassette according to application FR 2981154, even though this risk is minimal.

The general purpose of the invention is thus to mitigate some or all of the drawbacks of the prior art and especially to improve the cassette according to patent application FR2981154, and thus to propose a solution which guarantees the integrity of the sampling accomplished by a device for sampling and transporting of nano-objects liable to be present in an aerosol and to make sure of the traceability of the sampling up to the point of the elemental analysis proper, even in a situation where an unauthorized person might have adequate means for the opening of the cassette of the device in the assembled configuration.

It will be noted that elemental analysis is an analysis able to determine which atomic elements (titanium, carbon, nickel, etc.) are present, as well as their atomic percentage in the sample. On the other hand, an elemental analysis is not able to determine the structure or how these elements are assembled with one another.

One particular purpose of the invention is to propose a device of this kind which is simple to produce and low in cost.

EXPLANATION OF THE INVENTION:

To accomplish this, the invention first of all involves an assembly for sampling and transporting nano-objects liable to be present in an aerosol for the purposes of their analysis, comprising:
  a device comprising a porous sampling filter able to trap nano-objects liable to be in suspension in the aerosol, a cassette composed of a first piece and a second piece provided with means of mutual assembly and means of holding the filter, the first and second pieces in their assembled configuration defining a cavity in which the filter is lodged while being held, and at least one gasket able to produce tightness between the cavity and the outside, the means of mutual assembly comprising first clipping means integrated with the first piece, second clipping means integrated with the second piece and able to cooperate with the first means in order to bring about a clipping of the two pieces;
  a sampling apparatus comprising means of aspiration and a seat in which the cassette can be secured in a removable manner when the two pieces are in the assembled configuration to accomplish the sampling of the contaminants by means of aspiration.

According to the invention, the arrangement of the edges of the seat for fixation of the cassette relative to the clipping means is such that they cannot be reached physically, either manually or by a tool, even one adapted to their unclipping, in the assembled configuration of the pieces, when the cassette is in its configuration secured to the apparatus.

The phrase "not be accessible from the outside" means that the clipping means cannot be reached physically, either manually or by using an unclipping tool for the means of clipping of the pieces of the cassette from the space outside the device in the assembled configuration of the cassette, when it is in its configuration secured to the apparatus.

Thus, as compared to the sampling cassette according to patent application FR 2981154, the securing of the opening of the cassette is improved, since when it is secured to the apparatus even a tool adapted to unclipping the means of clipping of the pieces cannot physically reach these means.

The securing of the opening of the cassette according to the invention makes it possible to limit the risks of contamination of the filter. The sources of contamination can be classified into three categories, which can be enumerated as follows:
  a later contamination which might artificially increase the quantity of particles on the cassette (deposition),
  a decrease in the quantity of particles sampled on the filter (scraping);
  a pollution of a kind different than the one being sampled.

Moreover, the risk of contamination of the filter, the opening of the cassette by an unauthorized user, might result in an unfortunate exchanging of filters corresponding to different workers which would result in a wrong match-up of worker and filter and thus lead to a wrong monitoring of the exposure of the worker at his workstation. This break in the chain of traceability would compromise the monitoring of the exposure of the workers to nano-materials.

The invention makes it possible to strengthen this securing of the sampling: once inserted into its fixation seat on the apparatus, the cassette no longer allows the use of the tool to open it. The cassette first needs to be extracted from its seat. Thus, an unauthorized user who is nonetheless tempted to open the cassette would be forced to remove it from the apparatus to which it is secured. One may arrange that this will have the immediate consequence of halting the means of aspiration of the apparatus. Moreover, an appropriate detection system integrated in the apparatus, such as a sound and/or visual alarm, then allows a detecting of the unwanted removal of the cassette, and then interrupting of the sampling. Moreover, a registration of this interruption can then be done.

The solution according to the invention makes it possible to increase the compactness and robustness of the sampling cassette, of the production tooling for the cassette, as well as of the opening tool of the cassette, and allows their cost to be decreased. The reduction in size of the cassette is advantageous both from a standpoint of ergonomics and from one of handling or storage. The gain in terms of material cost is linked to the fact that a cassette according to the invention is more compact than a cassette according to patent application FR 2981154. This compactness implies a cost for the tooling to manufacture the cassette (injection molds) that is also lower than that of a cassette according to patent application FR 2981154.

The invention likewise deals with a sampling device for the assembly described above, wherein the means of holding the filter comprise two shoulders, one produced on an internal periphery of the first piece and the other on an internal periphery of the second piece, the device comprising a filter holder held by squeezing between the two shoulders.

According to one advantageous variant, at least one of the pieces comprises a notch running straight through the annular rim, the filter holder comprises a tongue that is complementary to the notch (or notches) and to which an identification element of the filter is secured, such that in the assembled configuration of the pieces and in the configuration of the cassette secured to the apparatus the identification element is in contact with the outer environment.

The phrase "in contact with the outer environment" means that the identification element energes into the space outside the device and the apparatus in the assembled configuration of the cassette when it is secured to the apparatus.

The identification element is preferably an electronic chip or a radiofrequency ID tag (RFID) or a two-dimensional barcode, of the Datamatrix® type. It may be secured by a gluing technique, by engraving, by overmolding or by tampography. The identification element may also be simply numbers and/or letters in order to be visible and read directly by a person.

In cumulative or alternative manner, one can provide an identification element of the filter constituted by at least one radiofrequency ID tag (RFID), the RFID tab(s) being lodged in the first and/or in the second piece. Preferably, the RFID tag can be lodged in the lower piece of the cassette. This variant has the advantage of preserving identification on the filter itself, and of being able to subject the filter to analyses which might alter the electronic circuit of a RFID tag. Specifically, by lodging a RFID tag in one and/or the other pieces of the cassette, there are no longer any electronics integrated directly in the filter and the filter holder, and thus an analysis undergone by the filter does not disrupt the electronic circuit of the tag. This also has the advantage of allowing the RFID chip to be brought closer to the sampling apparatus and thus of the transmission power of its antenna being reduced.

Preferably, the filter holder is deformable by compression in order to be flattened by the first and second pieces in the assembled configuration and thus form a single gasket.

One can provide at least one elastomer seal bearing against at least one of the shoulders.

The filter can be made of membranes made of alumina; silica, quartz or borosilicate fibers; cellulose or its derivatives such as methylcellulose (MCE); polyvinylidene fluoride (PVDF); polyestersulfone (PES); polystyrene (PS); polytetrafluoroethylene (PTFE); polycarbonate (PC). Generally, it is several micrometers to several tens of micrometers thick, for example, 10 to 200 micrometers. Typically, the filters have a thickness between 5 and 30 µm.

Advantageously, the first and second pieces and the filter holder are based on thermoplastic material, preferably polyethylene terephthalate (PET), polybutylene terephthalate (PBT), polymethyl methacrylate (PMMA), polyamide 6 (PA6), polyamide 66 (PA66), polycarbonate (PC), polypropylene (PP) or polyoxymethylene copolymer (POM-C).

According to one advantageous embodiment, the first clipping means are formed by a number equal to n of elastically deformable feet whose end comprises an opening and which are arranged on the first piece, being spaced apart by an angular position equal to it $2\pi/n$, and in that the second clipping means are formed by a same number n of protrusions of complementary shape to the openings and arranged on the second piece, being spaced apart by the same angular position equal to it $2\pi/n$ as the feet.

The invention further deals with a tool designed to perform the unclipping of the two pieces of the cassette, comprising pins which are spaced apart from each other by the same position as the protrusions and able to exert a thrusting on the latter, laterally to the longitudinal axis of the cassette.

The tool can further comprise means of mechanical guiding able to guide the tool underneath the piece provided with protrusions in order to facilitate the simultaneous lateral thrusting of the pins against the protrusions.

Finally, the invention deals with the use of an assembly as described above as an assembly for monitoring the exposure of workers at a manufacturing station for nano-objects, processing of nano-materials, or use of products containing them.

DETAILED DESCRIPTION

Other advantages and features will emerge more clearly from a perusal of the following detailed description, given as an illustration but not limited by this, making reference to the following figures, in which.

In order to carry out a sampling of nano-objects liable to be contained in an aerosol, the device according to the invention comprises first of all a filter, not shown, which is adapted to trap nano-objects liable to be in suspension in air, which is lodged and held in a cavity formed by a cassette in the closed configuration.

Thus, the sampling method according to the invention consists in orienting the closed cassette so that the air being analyzed is aspirated by a pump, not shown, which is integrated in a sampling apparatus 6 to which the cassette is attached, the air being aspirated from an orifice 20 and emerging from the cassette through an orifice 10 and then going to the pump.

The aspiration can of course be provided along a reverse path, that is, from the orifice 10 to the orifice 20. The nano-objects or particles of micrometer size so aspirated will be collected on the filter held in the cassette. In the method of sampling according to the invention, the cassette is oriented so that the sampling is as representative as possible of the respiration by being located less than 30 cm from the respiratory passages.

As is represented, the device according to the invention allows collecting of a sample and the transporting of the trapped nano-objects in a secured manner with perfect traceability.

The assembly for sampling and transporting of nano-objects according to the invention thus comprises the device with cassette and filter and the sampling apparatus 6 to which the cassette is secured during the sampling and which integrates the aspiration pump.

Figure 1:
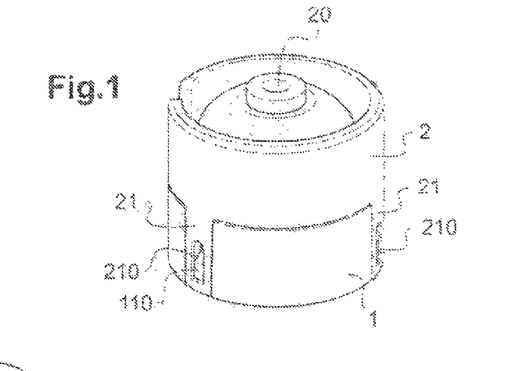
FIG. 1 is a profile view of the sampling cassette of a sampling device according to the invention, the cassette being in the assembled configuration.
Figure 1A:
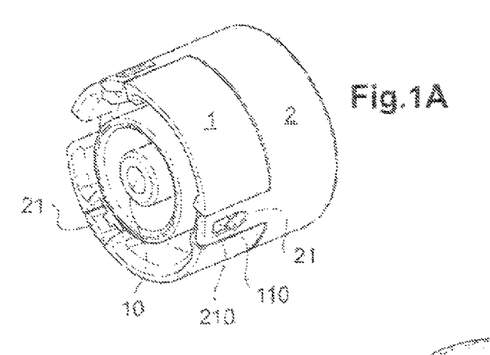
FIG. 1A is a bottom view of the cassette of FIG. 1.
Figure 2:
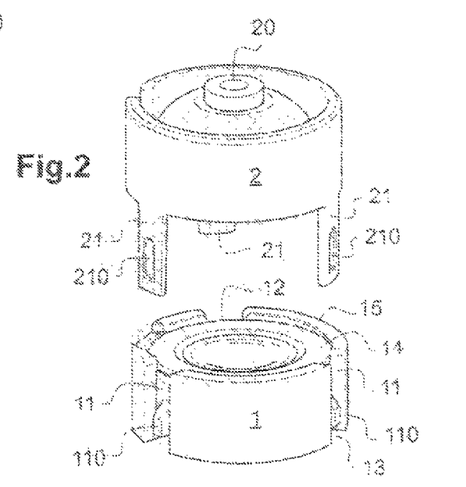
FIG. 2 is an exploded perspective view of the cassette of FIGS. 1 and 1A showing the two pieces of the cassette in non-assembled configuration.

As is illustrated in FIGS. 1 to 2, the cassette is composed of two pieces 1, 2 of general cylindrical shape.

The upper piece 2 is provided with feet 21 which are flexible, in other words elastically deformable, whose end comprises an opening 210.

The lower piece 1 is provided with cavities (or "channels") 11 which are individually complementary to a foot 21 with one end comprising a protrusion individually complementary to an opening 210. Of course, in the scope of the invention one can provide an arrangement of the complementary openings or protrusions in the reverse manner, that is, with protrusions individually in a cavity of the piece 2 and feet with openings on the piece 1.

The relative angular arrangement between flexible feet 21 of the upper piece 2 is identical to that of the cavities 11 of the lower piece 1.

Thus, in the mutual assembled configuration, the feet 21 with their openings 210 fit into and are clipped precisely in the cavities 11 and around the protrusions 110 (FIGS. 1A and 2).

Figure 4:
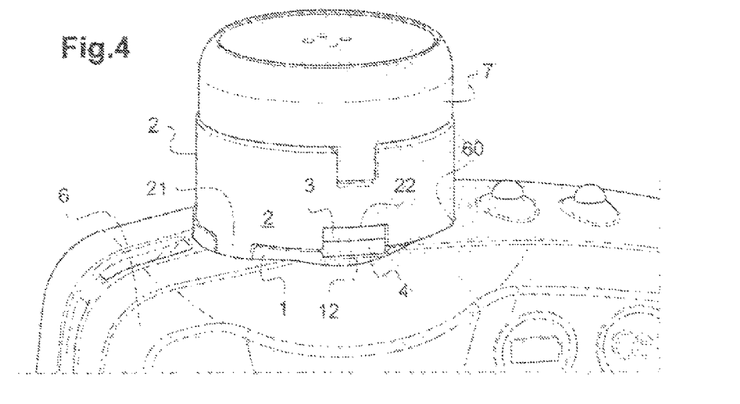
FIG. 4 is a perspective view showing a sampling assembly according to the invention with an apparatus integrating an aspiration pump and a cassette according to FIGS. 1 to 2 in a configuration secured to the apparatus.
Figure 4A:
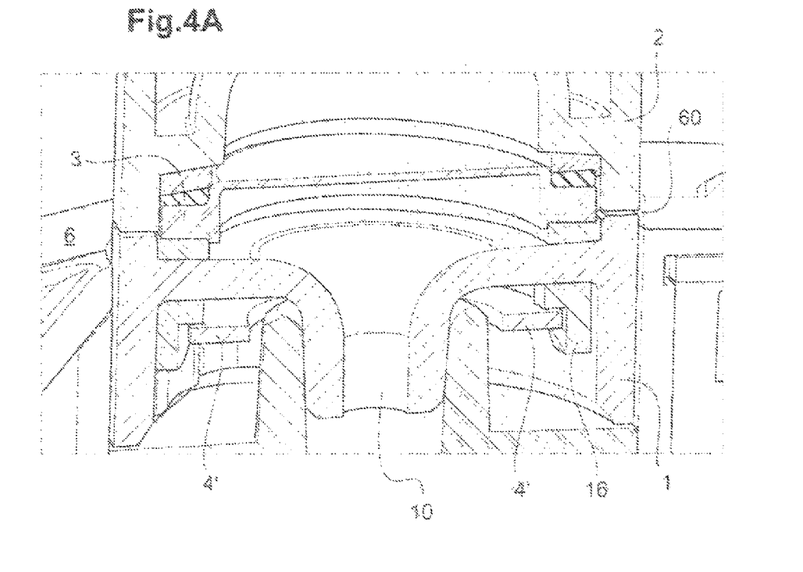
FIG. 4A is a detail sectional view of FIG. 4.

FIGS. 4 and 4A show the cassette with the pieces 1, 2 assembled together, such that it is secured to the sampling apparatus 6 integrating the aspiration pump for the contaminants.

As can be seen in these FIGS. 4 and 4A, in this mutually assembled configuration of the pieces 1, 2 and with the cassette secured to the apparatus 6, no clipping means 11, 110, 21, 210 is accessible from the outside, even with an adequate tool 5 as described hereafter enables the removal of the two pieces 1, 2. In other words, the arrangement of the edges of the seat for fixation 60 of the cassette relative to the clipping means is such that they cannot be reached physically, either manually or by a tool adapted to their unclipping.

Thanks to the invention, any untimely opening of the cassette outside of the analysis laboratory designated to analyze precisely the particles trapped on the filter is prevented.

Thus, as compared to the cassette according to patent application FR 2981154, the securing of the sampling is strengthened because the cassette once inserted in its fixation seat 60 on the apparatus does not even allow the use of the unclipping tool for the opening of the latter. The cassette first needs to be extracted from its seat. Thus, an unauthorized user who was nonetheless tempted to open the cassette would need to remove it from the apparatus to which it is secured. One may provide that this will have the immediate consequence of halting the means of aspiration of the apparatus. Moreover, an appropriate system of detection integrated in the apparatus, such as a sound and/or visual alarm, then allows for a detecting of the unwanted removal of the cassette, and an interrupting of the sampling process. Furthermore, a registration of this interruption can then be done.

One thus limits the risks of contamination of the latter, these not actually being representative of the sampling process and possibly occurring either due to decrease in the number of particles trapped on the filter (scraping) or adding of particles of a different nature than those being sampled.

As is better shown in FIG. 4A, in the configuration of the cassette 1, 2 secured to the sampling apparatus 6, the orifice 10 of the lower piece 1 of the cassette is in tight fluidic communication with the aspiration orifice 61 provided in the body of the sampling apparatus 6.

The lower piece 1 is provided with holes 13 emerging at the same time on the outside and in the zone where the protrusions 110 are arranged, that is, in the area of the zone where protrusions 110 cooperate by clipping with the feet 21 with their corresponding openings 210. There are therefore as many holes 13 as there are complementary clipping means.

The upper piece 2 has three flexible feet 21, positioned at 120° relative to each other, which fit precisely into the cavities 11 of the lower piece 1.

Once the sampling has been performed, the pump of the apparatus is halted and then the cassette is removed from its fixation seat 60 of the apparatus and then the sampling cassette is opened, that is, the unclipping of the two pieces 1,2 is done.

To perform the unclipping of the two pieces 1,2, one proceeds as follows.

Figure 3:
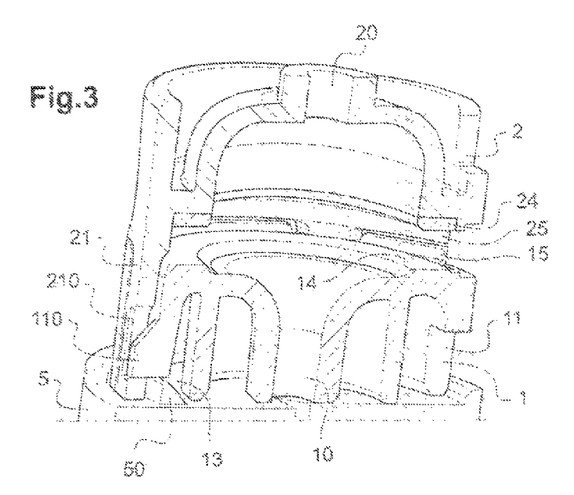
FIG. 3 is a sectional view of the cassette of FIGS. 1 to 2, further showing a tool according to the invention for the secured opening of the cassette.

First of all, the lower piece 1 of the cassette is placed on top of the tool 5 facing the pins 50.

Figures 6, 7, 8, 9:
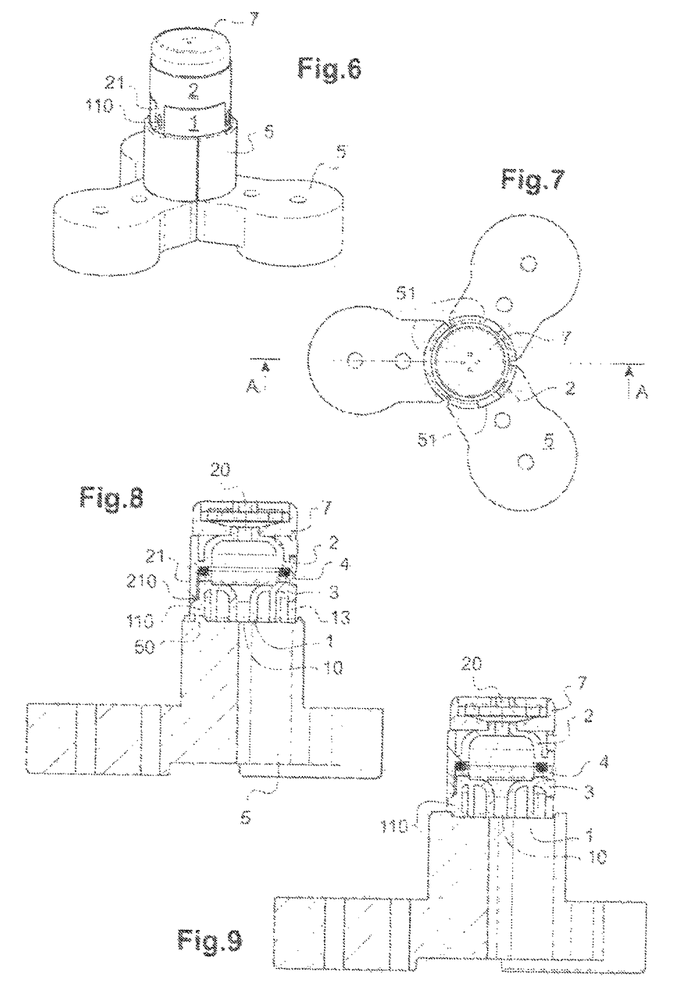
FIGS. 6 and 7 are respectively perspective and top views of the cassette according to FIGS. 1 to 2 mounted in its opening tool of its pieces.
FIGS. 8 and 9 are sectional views of FIG. 7 along A-A, respectively before and after opening of the pieces of the cassette.

One inserts into each hole 13 a pin 50 of sufficient length to reach the foot 21 in the position of its opening 210 clipped about a protrusion 110 (FIG. 8). Thus, an upward thrusting force on the pins 50 lodged in the holes 13 generates a lateral thrusting force on the feet 21 which then become unhooked from their corresponding protrusion 110, which dissociates the two pieces 1, 2 (FIG. 9).

Advantageously, all the pins 50 are secured to a tool 5 as shown in FIGS. 6 to 9, which likewise comprises rigid feet 51 spaced apart from each other to allow a seating of the cylindrical body of the lower piece 1. In other words, these rigid feet 51 serve as a guide to facilitate the simultaneous thrusting of the pins 50 against the feet 21.

Alternatively, the feet can be situated on the lower piece and the holes on the upper piece, without leaving the scope of the invention.

As for the filter, this is supported by a filter holder. In the assembled configuration of the two pieces 1, 2, the filter holder 3 is held squeezed between the two shoulders 14, 24 each produced on an internal periphery of one of the two pieces 1, 2.

Advantageously, the filter holder 3 is chosen from an elastically deformable material and it then plays a supplemental role of a gasket between the lower 1 and upper 2 pieces of the cassette. In other words, it is advantageously possible to provide a filter holder 3 with a lesser hardness than the materials of pieces 1 and 2 of the cassette, so as to be flattened against the opposite shoulders 14, 24, by pressure during the clipping process. As the filter holder 3 has the role of being a mechanical support for the filter, it can have an overall annular conformation or be made from a single massive piece traversed by a plurality of holes emptying via straight channels in the thickness of the piece, this plurality of holes then forming the filter proper.

In any case, one will make sure that it generates the minimum of head losses in the area of the aspiration.

According to one variant, the pieces 1, 2 of the cassette each comprise a notch 12, 22 running straight through the annular rim. The filter holder 3 comprises a tongue 4 that is complementary to the notches 12, 22 and on which an identification element of the filter can be produced, so that in the assembled configuration of the pieces and in the configuration of the cassette secured to the apparatus the identification element is in contact with the outer environment.

Figure 5:
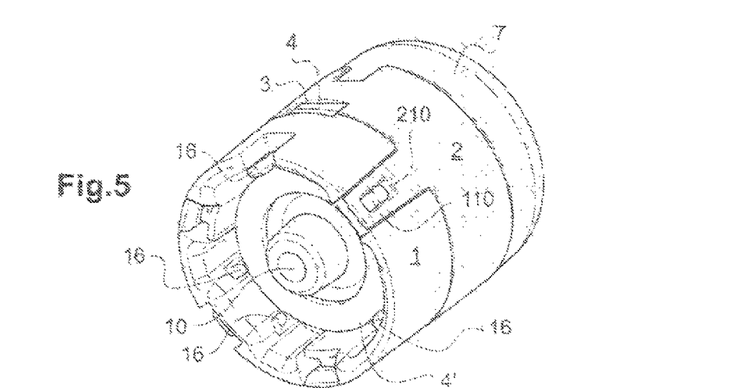
FIG. 5 is a bottom view of the cassette of FIG. 1 showing one variant for the integration of a RFID identification tag.

As illustrated in FIGS. 4A and 5, one can also provide an identification element of the filter composed of a radiofrequency identification (RFID) tag 4' which is seated in the lower piece 1 of the cassette. The securing of the RFID tag 4' can be done advantageously by clipping in holding feet 16 provided for this purpose in a portion of the lower piece 1 constituting a seat which is physically protected against the outside. This variant has the advantage of preserving an identification on the filter itself, and allowing the filter to be subjected to analyses which might alter the electronic circuit of the RFID tag 4'. Specifically, by seating a RFID tag 4' in the piece 1 of the cassette, there are no longer any electronics integrated directly in the filter and filter holder 3, and thus an analysis undergone by the filter does not disrupt the electronic circuit of the tag. This likewise has the advantage of allowing the RFID chip to be brought closer to the sampling apparatus and thus of reducing the transmission power of its antenna.

Depending on the needs, one can utilize in cumulative or alternative manner an identification element 4 and/or an identification tag 4'. For example, one may use a number and/or letter code 4 visible to the naked eye of a person from the outside and a tag 4' seated in the lower piece 1. One can also use only a number and/or letter code 4 or only a RFID tag 4'.

To further improve the mutual assembly of the two pieces 1 and 2, one can provide on each of them an annular rim 15, 25 in order to provide, in addition to the clipping, a mutual abutment surface between the pieces in their assembled position.

Advantageously, as illustrated in FIG. 4, a device to reduce the aspiration noise 7 is secured to the upper piece 2, as is described and claimed in the patent application filed today by the applicant and entitled "Device for sampling and transporting of nano-objects contained in aerosols, with a cassette with a module suited to reducing the suction noise during the sampling".

Other variants and improvements can be made without thereby leaving the scope of the invention.

The invention is not limited to the examples just described; in particular, one can combine the features of the examples illustrated in the context of variants which have not been illustrated.

The invention claimed is:

1. An assembly for sampling and transporting of nano-objects present in an aerosol for analysis, comprising:
   a device comprising:
      a porous sampling filter configured to trap nano-objects in suspension in the aerosol,
      a cassette composed of a first piece and a second piece provided with means for holding the filter, the first and second pieces, in an assembled configuration, defining a cavity in which the filter is held, wherein:
         the first piece comprises at least one elastically deformable foot extending from the first piece and comprising an opening, and
         the second piece comprises at least one channel configured to receive the at least one elastically deformable foot, and a protrusion extending radially from the at least one channel and configured to engage the opening of the deformable foot when the first and second pieces are in the assembled configuration, and
      at least one gasket configured to produce tightness between the cavity and an environment external to the cavity;
   a sampling apparatus comprising means of aspiration and a seat defining a seat opening for receiving the cassette, wherein:
      the cassette is secured in the seat opening in a removable manner when in the assembled configuration to accomplish sampling of contaminants by the means of aspiration, and
      when in the assembled configuration and when the cassette is secured in the seat opening, the at least one elastically deformable foot extends at least partly in seat opening and the seat prevents disengagement of the opening of the at least one elastically deformable foot from the protrusion of the at least one channel.

2. The assembly for sampling and transporting as claimed in claim 1, wherein the means for holding the filter comprises two shoulders, one shoulder disposed on an internal periphery of the first piece and another shoulder disposed on an internal periphery of the second piece, the device comprising a filter holder held by squeezing between the two shoulders.

3. The assembly for sampling and transporting as claimed in claim 1, wherein at least one of the first piece and the second piece comprises a notch running straight through an annular rim, a filter holder comprising a tongue that is complementary to the notch and to which an identification element of the filter is secured, such that in the assembled configuration of the first and second pieces and in the configuration of the cassette secured in the seat opening, the identification element is in contact with the external environment.

4. The assembly for sampling and transporting as claimed in claim 1, wherein the filter comprises an identification element comprising at least one radiofrequency ID tag (RFID), the at least one RFID tag being lodged in the first piece and/or in the second piece.

5. The assembly for sampling and transporting as claimed in claim 1, wherein the at least one channel comprises a number n of the at least one channel and a corresponding number of the at least one elastically deformable foot,
   wherein the number n of the at least one channel and corresponding number of the at least one elastically deformable foot are arranged on the second piece and first piece, respectively, and spaced apart by an angular position equal to $2\pi/n$.

6. The assembly for sampling and transporting as claimed in claim 1, wherein the sampling apparatus comprises means for commanding stoppage of the means of aspiration in response to removal of the cassette during a sampling process.

7. The assembly for sampling and transporting as claimed in claim 6, wherein the sampling apparatus comprises visual and/or audio feedback generated in response to removal of the cassette during a sampling process.

* * * * *